United States Patent
Laumer et al.

(10) Patent No.: US 8,337,772 B2
(45) Date of Patent: Dec. 25, 2012

(54) DEVICE FOR STERILIZING CONTAINERS

(75) Inventors: Roland Laumer, Regensburg (DE);
Manfred Schmid, Aufhausen (DE);
Berthold Burgmeier,
Dischingen/Eglingen (DE)

(73) Assignee: Krones AG (DE)

( * ) Notice: Subject to any disclaimer, the term of this patent is extended or adjusted under 35 U.S.C. 154(b) by 224 days.

(21) Appl. No.: 12/681,426

(22) PCT Filed: Sep. 30, 2008

(86) PCT No.: PCT/EP2008/063090
§ 371 (c)(1),
(2), (4) Date: Jun. 17, 2010

(87) PCT Pub. No.: WO2009/047171
PCT Pub. Date: Apr. 16, 2009

(65) Prior Publication Data
US 2010/0266467 A1    Oct. 21, 2010

(30) Foreign Application Priority Data
Oct. 2, 2007    (DE) .......................... 10 2007 047 259

(51) Int. Cl.
*A61L 2/00* (2006.01)
*B01J 19/00* (2006.01)

(52) U.S. Cl. ....................... 422/302; 422/291

(58) Field of Classification Search .................. 422/291, 422/302
See application file for complete search history.

(56) References Cited

U.S. PATENT DOCUMENTS

| 5,518,617 | A * | 5/1996 | Timmons | 210/519 |
| 7,341,079 | B2 | 3/2008 | Zanga | 141/92 |
| 7,404,276 | B2 | 7/2008 | Till et al. | 53/136.1 |
| 2006/0059862 | A1 * | 3/2006 | Zanga | 53/319 |
| 2007/0204562 | A1 * | 9/2007 | Till et al. | 53/167 |

FOREIGN PATENT DOCUMENTS

| EP | 1 601 606 | 12/2005 |
| EP | 1 821 010 | 8/2007 |
| GB | 407672 | 3/1934 |
| WO | WO 2004/065283 | 8/2004 |

* cited by examiner

Primary Examiner — Kevin Joyner
(74) Attorney, Agent, or Firm — Hayes Soloway P.C.

(57) ABSTRACT

A device for sterilizing containers includes a first treatment space, which is filled with a sterilizing gaseous medium under predetermined thermodynamic conditions, a tank, which is filled with a liquid medium and extends along a closed path, and a multiplicity of holding devices for holding the containers. The holding devices are arranged rotatably with respect to the treatment space, and a dividing wall, which protrudes into the liquid medium located in the tank is arranged rotatably with respect to the tank. A discharge opening, via which the gaseous medium can be discharged, is provided between the treatment space and the tank.

19 Claims, 4 Drawing Sheets

DEVICE FOR STERILIZING CONTAINERS

BACKGROUND OF THE INVENTION

The present invention relates to a device for sterilizing containers and in particular plastic bottles. However, it is pointed out that the present invention is also applicable to other treatments of containers, such as for example to the closing or also the production or cleaning of containers.

Many such devices are known from the prior art. It is known inter alia to disinfect the containers using a hydrogen peroxide gas. In one device known from the prior art, the containers are guided by a circular transport carousel through a sterilization chamber and are disinfected by a hydrogen peroxide-containing gas within this sterilization chamber. In such devices, the problem occurs that any escape of this hydrogen peroxide-containing gas must be prevented as efficiently as possible, since such gases are harmful to users.

The present invention is applicable both to devices which bring about a sterilization of the inner wall of the containers and to devices which carry out a sterilization of the outer wall of the containers. Furthermore, the invention is also suitable for devices which fill the containers with a beverage in a sterile environment.

It is known in the prior art to use so-called water locks to prevent any escape of the gas from the device. In this case, a liquid is passed into a stationary tank and an element of the rotating transport carousel, which also carries the containers for example, constantly slides through this liquid. In this way, on the one hand a rotation is possible and on the other hand the gas cannot escape at this liquid barrier. In other words, this water lock forms a rotatable sealed connection or a liquid bath forming a hydraulic seal.

An apparatus for the septic conditioning of various products is known from DE 2 139 057. This apparatus comprises a chamber which is sealed off from the external atmosphere by a cupola. Furthermore, a rotatable sealed connection to a liquid bath forming a hydraulic connection is provided.

A machine for the aseptic treatment of containers in a bottling plant is known from EP 1 601 606 B1. Here, too, two annular shaped tanks filled with liquid are provided, in which in each case annular bodies slide so as in this way to achieve sealing. The two tanks filled with liquid directly adjoin the sterile chamber in this case.

One object of the present invention is to increase the safety of such devices with regard to the escape of the sterilizing medium. Another object is to simplify the devices known from the prior art.

SUMMARY OF THE INVENTION

A device according to the invention for sterilizing containers comprises a treatment chamber which is filled with a sterilizing gaseous medium under predefined thermodynamic conditions, and in particular at a predefined pressure, a tank which is filled with a liquid medium and extends along a closed path, and a plurality of holding devices for holding the containers, wherein the holding devices are arranged such as to be able to rotate relative to at least one of the walls forming the treatment chamber. Also provided is a separating wall which protrudes partially into the liquid medium located in the tank and is arranged such as to be able to rotate relative to the tank. The separating wall is in this case connected to the holding devices, in particular so as to be secured in rotation therewith. According to the invention, a discharge opening, via which the gaseous medium can be discharged, is provided between the treatment chamber and the liquid medium located in the tank.

In this case, it is possible on the one hand that the discharge opening is arranged outside the outer wall of the tank. However, it would also be possible that the discharge opening is arranged above a fill level of the liquid medium located in the tank (and therefore possibly still inside the tank or inside the cavity formed by the walls of the tank).

In both configurations, the discharge opening would therefore by definition be provided between the tank and the treatment chamber. The term "between" is therefore understood with reference to the space which is located between the tank, and in particular the liquid located in this tank, and the treatment chamber.

The sterilizing medium is preferably hydrogen peroxide or a hydrogen peroxide-containing gas. The liquid medium is in particular water and particularly preferably a bacteriostatic solution. The separating wall preferably protrudes into the liquid medium in such a way that the liquid medium together with the separating wall acts as a seal which seals off the treatment chamber from the surrounding environment. The combination of the tank containing the liquid medium and the separating wall forms the abovementioned "water lock".

Preferably, the tank containing the liquid is substantially circular and the treatment chamber is thus in particular a sterile treatment chamber.

By virtue of the discharge opening according to the invention, a pressure balance can be formed between the water lock and the treatment chamber and thus any escape of gaseous medium in an undesirable manner, i.e. in any other way, can be avoided in a particularly reliable manner.

Preferably, a buffer chamber for the gaseous medium is provided between the treatment chamber and the liquid medium located in the tank. It is pointed out that it would also be possible to provide just the buffer chamber, and not the abovementioned discharge opening. The applicant reserves the right to direct a corresponding claim towards a device comprising the aforementioned buffer chamber. Preferably, the gaseous medium in the buffer chamber is at a lower pressure than in the treatment chamber. With particular preference, however, the pressure of the tank in the buffer chamber is greater than the (atmospheric) external pressure.

By virtue of this pressure drop between the treatment chamber and the buffer chamber, the gaseous medium always passes from the treatment chamber into the buffer chamber. In this way, the treatment chamber can always be kept as a sterile chamber. The buffer chamber, on the other hand, is preferably not designed as a sterile chamber.

Preferably, the separating wall is arranged on a cover which covers the treatment chamber. More specifically, the holding devices for the containers are also arranged so as to be secured in rotation with this cover.

In a further advantageous embodiment, the treatment chamber is bounded by a stationary side wall and a side wall which can rotate relative to the stationary side wall. This configuration allows a particularly efficient sealing of the sterile treatment chamber. Preferably, the device comprises two tanks of the type described above, into which respectively the abovementioned separating walls protrude. In this case, preferably the two tanks are in each case arranged in a stationary manner, and the two separating walls rotate relative to these tanks. In a further advantageous embodiment, the separating walls are connected to the abovementioned cover so as to be secured in rotation therewith.

In a further advantageous embodiment, one of these tanks is arranged below the containers to be sterilized, or the carrier devices thereof, and the other tank is arranged above the containers to be sterilized. In this way, complete sealing of the treatment chamber can be achieved. In this case it is possible to provide buffer chambers of the type described above for each of the two tanks filled with the liquid medium, and also to provide discharge openings in both cases, via which the gaseous medium can be discharged.

Preferably, the tank comprises a radially outer boundary wall and a radially inner boundary wall, and the radially outer boundary wall is higher than the radially inner boundary wall. In this way, the tank can be filled for cleaning purposes in such a way that the cleaning agent flows inwards relative to the tank. The tanks are in particular channels shaped as a ring or as a segment of a ring.

In a further advantageous embodiment, provided between the treatment chamber and the buffer chamber are at least two deflecting walls which deflect a flow direction of the gaseous medium towards the discharge opening. Due to the lower pressure in the buffer chamber, the gaseous medium flows from the treatment chamber into the buffer chamber and is deflected in the process by the deflecting walls. In this case, preferably one deflecting wall is arranged in a stationary manner and the other deflecting wall is arranged such as to be able to rotate relative to this stationary deflecting wall.

Preferably, the cover is arranged in a rotatable manner.

In a further advantageous embodiment, at least one nozzle for cleaning the buffer chamber is provided on the cover. Preferably, a plurality of nozzles are distributed in the circumferential direction and advantageously also in the radial direction. In a further advantageous embodiment, a nozzle for cleaning the intermediate space between the at least two deflecting walls is also provided.

Advantageously, at least one nozzle for cleaning the tank is also provided on the tank. It is thus also possible to clean the abovementioned "water lock". Preferably, this nozzle also serves for filling this tank.

In a further advantageous embodiment, at least one nozzle arranged in a stationary manner is also provided in the buffer chamber. Preferably, this nozzle is arranged in a bottom section of the buffer chamber.

Preferably, the tank containing the liquid is arranged below the containers to be sterilized. However, it would also be possible that the tank is provided above the containers to be sterilized, or that, as mentioned, two such tanks are provided.

In a further advantageous embodiment, the discharge opening is arranged above a fill level of the liquid medium. With particular preference, the discharge opening is in this case adjoined by a discharge pipe for the gaseous medium, which extends partially through the tank. Advantageously, the discharge pipe extends at least partially through the liquid located in the tank.

By virtue of this embodiment, there is no need for an additional buffer chamber which is formed between the outer wall of the tank and the treatment chamber. The buffer chamber is in this case preferably formed above the liquid medium.

BRIEF DESCRIPTION OF THE DRAWINGS

Further advantages and embodiments will emerge from the appended drawings.

In the drawings.

DETAILED DESCRIPTION OF THE INVENTION

Figure 1:
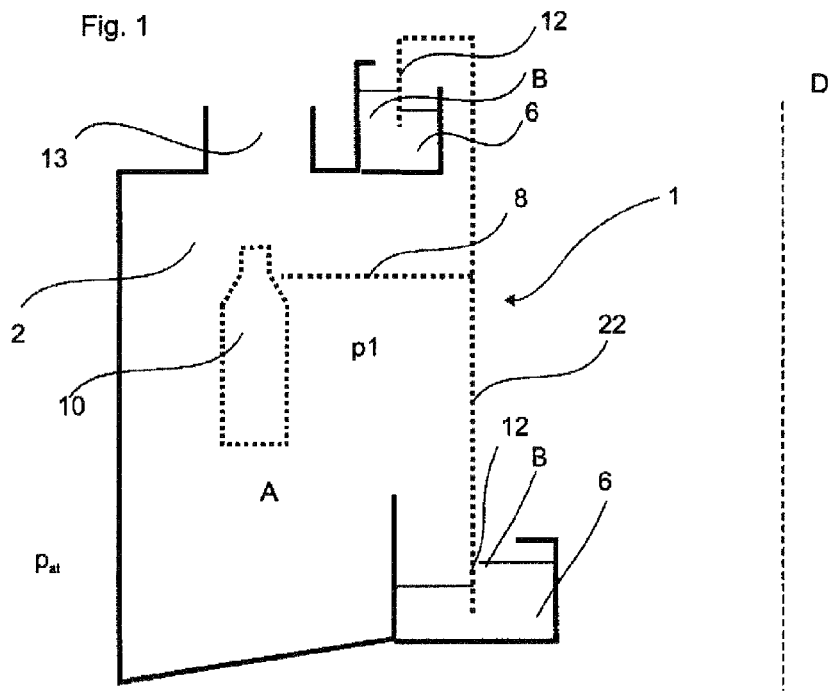
FIG. 1 shows a schematic view of a device for sterilizing containers.

FIG. 1 shows a device 1 for sterilizing containers. This device comprises a treatment chamber 2, through which containers 10 are guides for sterilization purposes. This treatment chamber 2 is formed partly by stationary components and partly by components which rotate relative to those stationary components. In FIG. 1, the stationary components are shown by unbroken lines and the components which rotate thereto are shown by broken lines.

A sterile gas is introduced into the treatment chamber 2 via an inlet opening 13. In order to seal off the rotating components relative to the stationary components, two tanks are provided which are in each case filled with a bacteriostatic solution or for example with water. This solution is denoted by reference B. In each case a separating wall 12 protrudes both into the lower tank 6 and into the upper tank 6, namely in such a way that this separating wall 12 dips into the liquid B. The treatment chamber 2 as a whole is sealed off as a result of this separating wall dipping into the two tanks 6. Reference 8 denotes a carrier device which guides the containers 10 through the treatment chamber 2.

A first pressure p1 prevails inside the treatment chamber, and an atmospheric pressure $P_{at}$ which is lower than the pressure p1 prevails outside the treatment chamber.

Due to these pressure differences, the fill levels of the liquid medium B are not balanced, but rather the liquid level on the side of the separating wall 12 protruding into the treatment chamber 2 is in each case lower than the liquid level on the side of the separating wall 12 located outside the treatment chamber 2. The rotatable units of the device 1 are in this case rotatable about an axis of rotation D. The two tanks 6 extend in the shape of a (segment of a) ring likewise around this axis of rotation D. The treatment chamber 2 also extends around the axis of rotation D in the shape of a (segment of a) circular ring.

Figure 2:
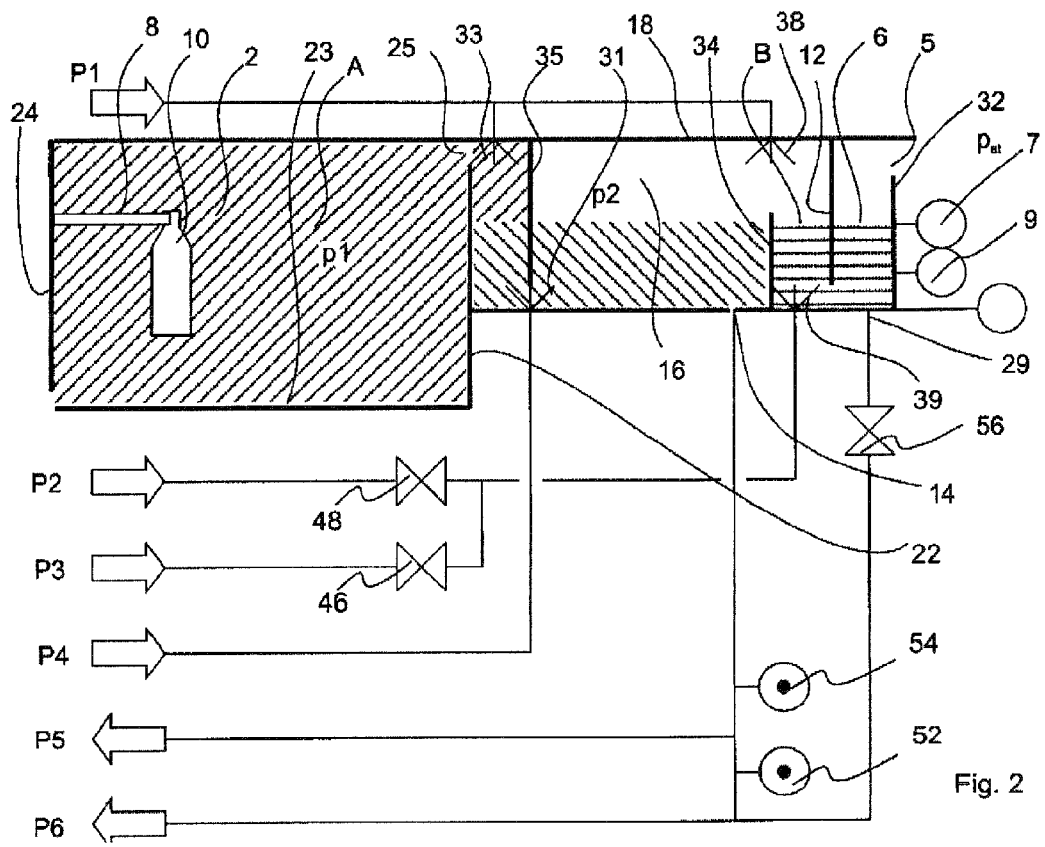
FIG. 2 shows a partial view of a device according to the invention for sterilizing containers.

FIG. 2 shows a detail view of a device according to the invention for sterilizing containers. Here, too, the containers 10 are guided at least partially along a circular path through a treatment chamber 2. In this case, the containers 10 are arranged on holding devices 8. The holding devices 8 are in turn attached to a side wall 24 which bounds the treatment chamber 2. During ongoing operation, a sterile medium A is provided in the treatment chamber 2. FIG. 2 shows only one tank 6 which is filled with the solution B. A further tank (not shown) serves to seal off the space between the wall 24 and the (stationary) bottom 23.

Reference 18 denotes the cover which covers the treatment chamber 2. Also provided on this cover 18 is a separating wall 12 which, as discussed above, protrudes into the tank 6 and the solution B. A discharge opening 14 is provided between the treatment chamber and the tank 6. Via this discharge opening 14, the gaseous medium can be discharged during ongoing operation. Reference 16 denotes a buffer chamber for the gaseous medium A. Due to the discharge opening 14, it is achieved that a pressure p2 prevails within this buffer chamber 16 which is lower than the pressure p1 in the treatment chamber 2, but higher than the atmospheric pressure $p_{at}$ outside the device. Reference 35 denotes a deflecting wall which thus forms a labyrinth, along which the pressure p1 prevailing in the treatment chamber 2 can be decreased to the pressure p2 prevailing in the buffer chamber 16.

Reference 22 denotes a further (stationary) side wall which bounds the treatment chamber 2. The treatment chamber 2 is thus bounded by the two side walls 22 and 24, the bottom 23 and the cover 18. Formed between the cover 18 and the side wall 22 is an opening or a gap 25, through which the gaseous medium A passes out of the treatment chamber 2. The highest flow rate of the gaseous medium occurs at this (annular) gap 25. A sterile boundary between the clean chamber and the surrounding environment can thus be defined at this annular gap.

Reference 5 denotes an outlet for in particular air, in order to permit a pressure equalisation between the buffer chamber 16 and the outer area of the device. References 7 and 9 denote fill level measuring devices which determine a fill level of the liquid medium B within the tank 6. It is also possible that the container can be refilled in reaction to an excessively low fill level. The tank 6 is bounded in the radial direction by a first boundary wall 32 and a second boundary wall 34. In this case, the inner boundary wall 34 is lower than the outer boundary wall 32. This has the advantage that the tank 6 can be filled in such a way that the liquid medium B passes into the buffer chamber 16 in order also to be able to clean the latter.

References 31, 33 and 38 denote nozzles which serve for internal cleaning of the device 1. Here, the two nozzles 33 and 38 are arranged on the rotatable cover 18 and, as shown in FIG. 2, clean the area to the left and to the right of the deflecting wall 35. The nozzle 31 is arranged in a stationary manner and serves for internal cleaning of the buffer chamber 16. Furthermore, a nozzle 39 is provided in the tank 6 for the internal cleaning of the latter. Reference 29 denotes an outlet opening, via which the liquid medium B can be discharged from the tank. The lower nozzles 31, 39 thus clean the stationary part of the annular channels and the nozzles 33 and 38 clean the rotating part thereof.

References 46, 48 and 56 denote different valves, the function of which will be explained in more detail below. During ongoing operation, the two valves 46 and 48 are closed. Via an inlet (not shown), the gaseous medium enters the treatment chamber 2 and is discharged in a defined manner via the discharge opening 14 in the direction of the arrow P6. References 52 and 54 denote diaphragms which serve as water separators so as to be able if necessary to convey away any liquid which passes through the discharge opening 14.

If the fill level of the liquid medium B drops below a certain level, the valve 48 can be opened and the tank 6 can be refilled with the liquid medium B via the nozzle 39. During so-called CIP cleaning (cleaning in place), a cleaning agent passes through the nozzle 33 in the direction of the arrow P1 into the second buffer chamber 16 in order to clean the interior thereof. Similarly, the cleaning agent passes through the nozzle 39 in the direction of the arrow P2 into the tank 6 and also through the nozzle 31 in the direction of the arrow P4 into the buffer chamber 16. After this cleaning, the tank 6 can also once again be filled with the liquid medium.

In the embodiment shown in FIG. 1, the valves provided below the treatment chamber 2 are arranged in a stationary manner.

Furthermore, it is also possible to open the valve 56 and to drain the liquid medium or also the cleaning agent from the tank 6. Hydrogen peroxide or a hydrogen peroxide-containing mixture can be introduced into the buffer chamber 16 in the direction of the arrow P4.

For SIP cleaning (sterilization in place), the buffer chamber 16 can once again be filled with a sterilization medium via the nozzles 31, 33 and 38 and at the same time this medium can be drained off again via the discharge opening 14. Non-sterile gaseous medium is located in the buffer chamber 16 and, as mentioned above, the sterile medium A is located in the treatment chamber 2.

In the embodiment shown in FIG. 2, two tanks 6 could also be arranged next to one another (or concentrically relative to one another). More specifically, in addition to the tank shown in FIG. 2, an inner second tank containing a corresponding separating wall 12 could also be provided. This inner tank could in this case be filled with a sterilizing medium and could seal off the treatment chamber from the buffer chamber 16, whereas the tank shown in FIG. 2 could be filled with water in order to seal off the buffer chamber 16 from the surrounding environment. In this way, it would be possible to prevent even more efficiently any escape of aggressive gases from the buffer chamber. Furthermore, by virtue of such redundant seals, it would be possible to maintain the overall sealing effect even in the event of failure of a seal. Also in the further embodiments shown in the context of this disclosure, two tanks could be provided next to one another.

Figure 3:
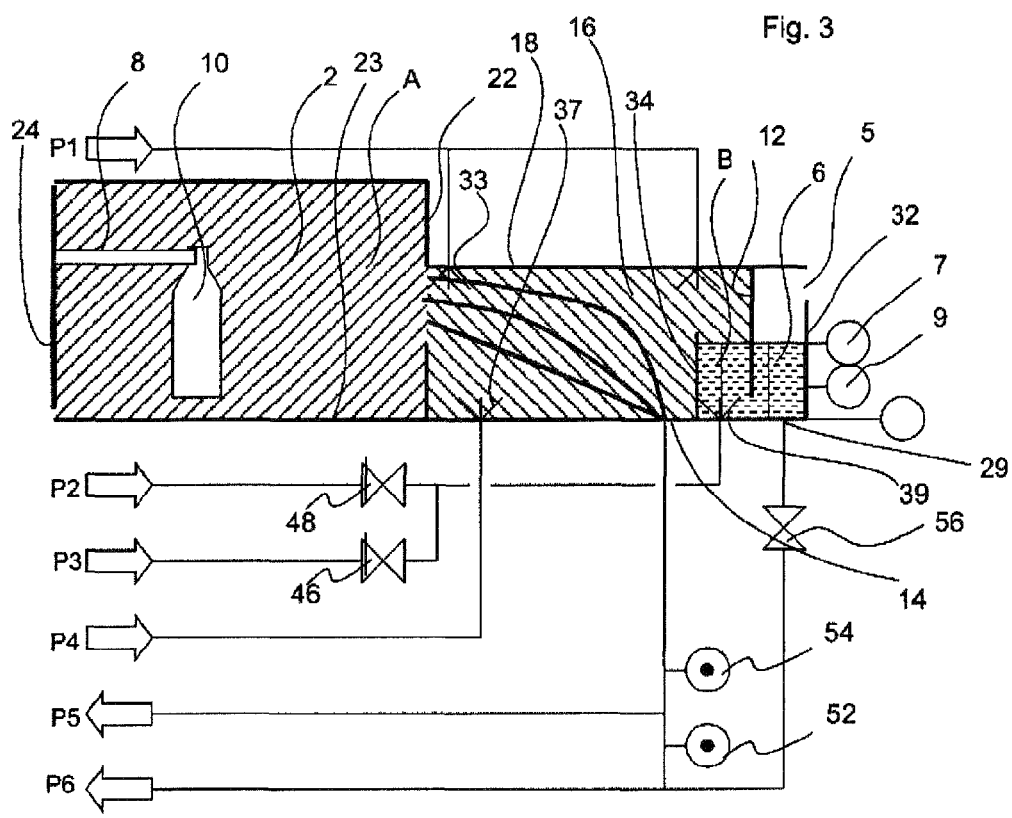
FIG. 3 shows a further partial view of a device according to the invention for sterilizing containers.

FIG. 3 shows a schematic view of a lower seal, i.e. a seal which is arranged below the containers to be sterilized. In contrast to the seal shown in FIG. 2, in the case of the seal shown in FIG. 3 between the treatment chamber 2 and the buffer chamber 16 the flow of the medium is not deflected multiple times. Apart from this, the arrangement of the lower seal largely corresponds to the arrangement of the upper seal and will therefore not be explained in any further detail. The gaseous medium A passes in the direction of the unbroken lines from the treatment chamber 2 towards the discharge opening 14.

Figure 4:
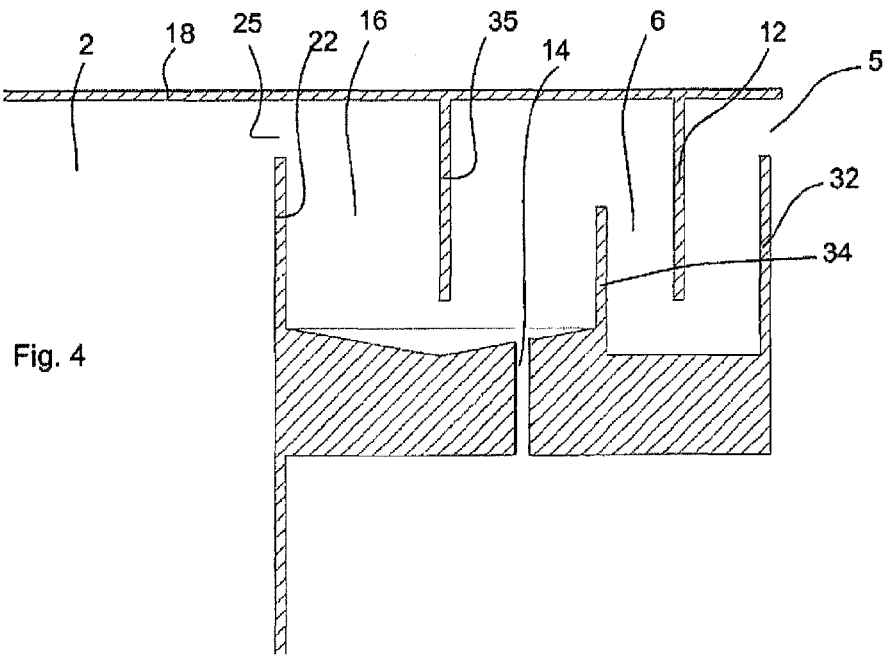
FIG. 4 shows a detail view of an upper sealing device.

FIG. 4 shows a detailed view of an upper seal. It is possible to see in particular also the tank 6 or the water lock and also the hydrogen peroxide barrier arranged to the left of the tank 6 in the figure and the buffer chamber 16 with the discharge opening 14.

Figure 5:
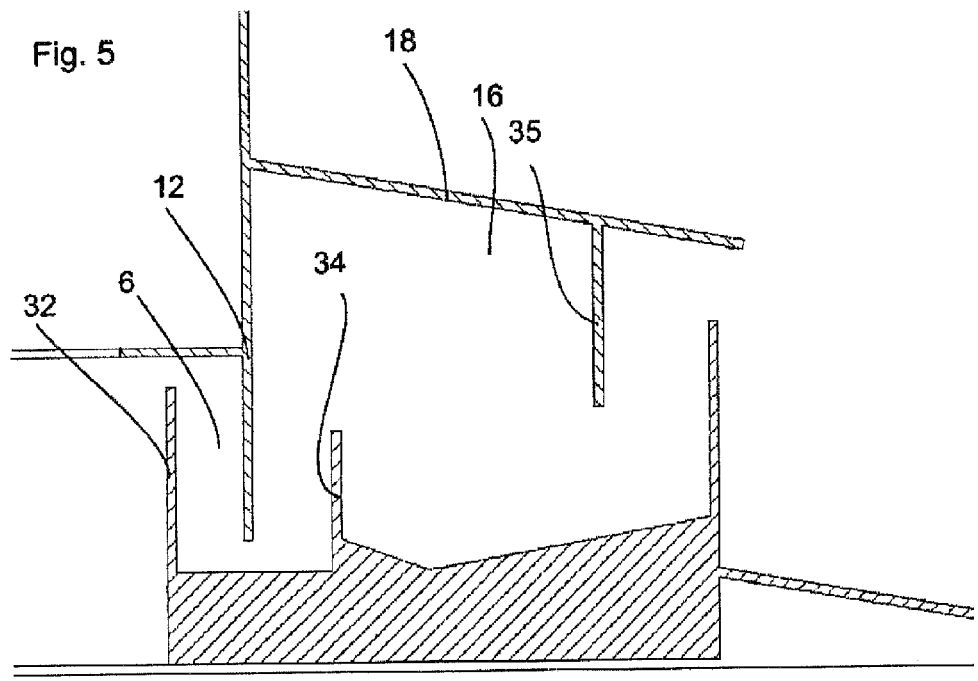
FIG. 5 shows a detailed view of a lower sealing device.

FIG. 5 shows a view of the lower seal. In this lower seal, too, a discharge opening (not shown) for the gaseous medium A can be provided in a buffer chamber 16.

Figure 6:
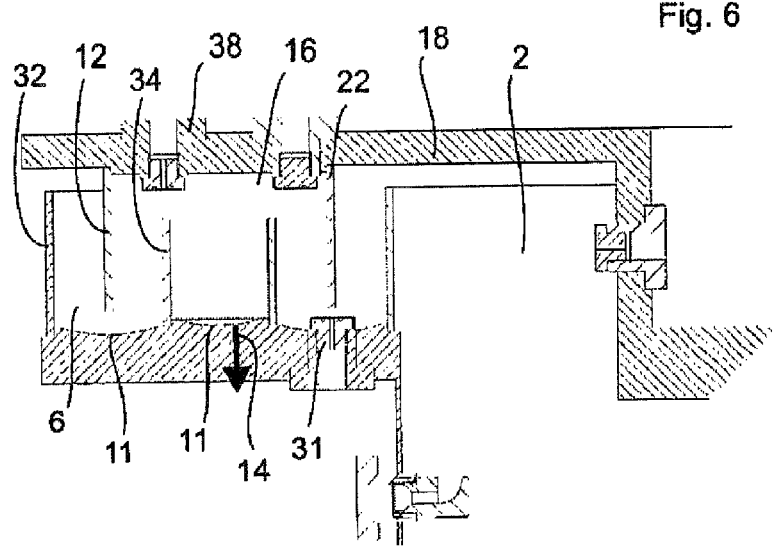
FIG. 6 shows a further detail view of a device according to the invention.

FIG. 6 shows a more detailed view of an upper seal. It is possible to see here depressions or cavities 11 which serve in particular for collecting liquid from cleaning fluid. Here, too, reference 31 denotes a nozzle which serves for introducing a medium into the buffer chamber 16. The arrow P8 illustrates the gaseous medium A exiting via the discharge opening during ongoing operation.

Figure 7:
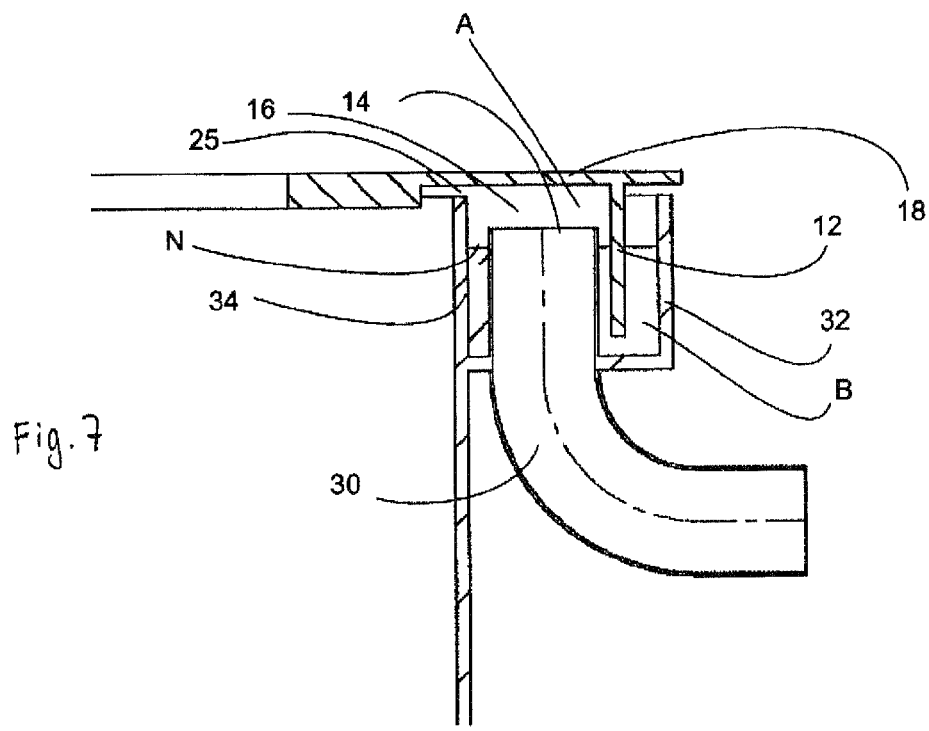
FIG. 7 shows a detail view of a device according to the invention in a further embodiment.

FIG. 7 shows a detail view of a further embodiment of the device according to the invention. While in the embodiments shown in the previous figures the discharge opening 14 is arranged outside the tank 6 or between the wall 34 of the tank 6 and the treatment chamber 2, in the embodiment shown in FIG. 7 it is provided between the two walls 34 and 32, but above a fill level N of the tank 6. More specifically, the discharge opening 14 is provided between the separating wall 12 and the wall 34.

Here, the buffer chamber 16 is above the liquid medium B on the left-hand side relative to the separating wall 12. Reference 30 denotes a discharge pipe, at the end of which the discharge opening 14 is located. This discharge pipe 30 extends from a bottom 27 of the tank 6 essentially vertically upwards and thus through the liquid B. Below the bottom 27 there is curved section of the pipe 30.

In the embodiment shown in FIG. 7, the discharge opening 14 is arranged lower than the upper ends of the two walls 32, 34. In this way, it is possible for excess liquid to be conveyed away via the discharge opening 14. However, it would also be possible to provide a closure mechanism (not shown, for example by using a float) which causes the discharge opening to close when the fill level N rises to the height of the discharge opening 14.

FIG. 7 thus shows a particularly space-saving embodiment. Above the liquid level N, a further annular channel is obtained, in which a negative pressure prevails. Here, too, the highest flow rate is obtained at the (annular) gap 25.

Figure 8:
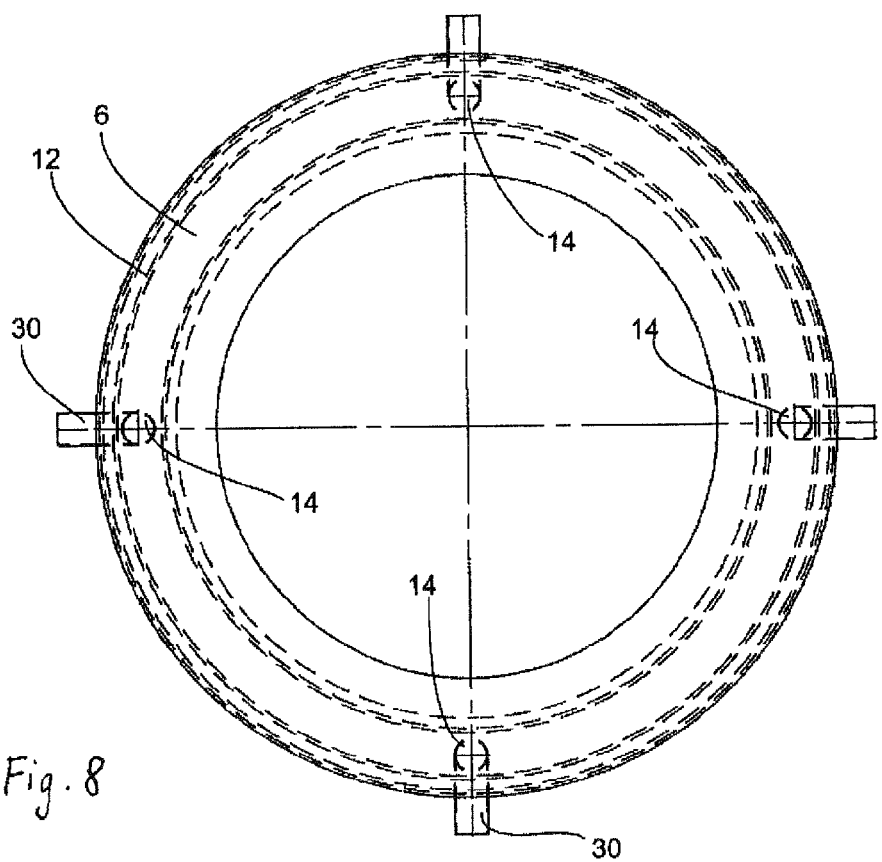
FIG. 8 shows a plan view of the device of FIG. 7.

FIG. 8 shows a plan view of a device from FIG. 7. It can be seen that here a total of four discharge openings 14 are arranged within the tank 6. These four discharge openings 14 are evenly distributed in the circumferential direction. The discharge openings 14 have a cross section which is slightly smaller than the radial distance between the separating wall 12 and the wall 34 of the tank 6.

The entire sealing system is advantageously inserted between a carrier plate of the device and a housing of the clean chamber.

All of the features disclosed in the application documents are claimed as essential to the invention in so far as they are novel individually or in combination with respect to the prior art.

The invention claimed is:

1. A device for sterilizing containers, comprising a treatment chamber which is filled with a sterilizing gaseous medium under predefined thermodynamic conditions, a tank which is filled with a liquid medium and which extends along a closed path, a plurality of holding devices for holding the containers, wherein the holding devices are rotatable relative to at least one of the walls forming the treatment chamber, and a separating wall which protrudes into the liquid medium located in the tank and rotatable relative to the tank, wherein a discharge opening located below a fill level of the liquid medium, via which the gaseous via which the gaseous medium can be discharged, is provided between the treatment chamber and the liquid medium located in the tank, and wherein a buffer chamber for the gaseous medium is provided between the treatment chamber and the liquid medium located in the tank, wherein the medium in the buffer chamber is maintained at a lower pressure than in the treatment chamber such that the gaseous medium passes from the treatment chamber into the buffer chamber.

2. The device according to claim 1, wherein the separating wall is arranged on a cover which covers the treatment chamber.

3. The device according to claim 2, wherein the cover is arranged in a rotatable manner.

4. The device according to claim 2, wherein at least one nozzle for cleaning the buffer chamber is provided on the cover.

5. The device according to claim 1, wherein the treatment chamber is bounded by a stationary side wall and a rotatable side wall which can rotate relative to the stationary side wall.

6. The device according to claim 1, wherein the device comprises two tanks which are separated from one another and also two separating walls, which respectively protrude into the tanks.

7. The device according to claim 1, wherein the tank comprises a radially outer boundary wall and a radially inner boundary wall, and the radially outer boundary wall is lower than the radially inner boundary wall.

8. The device according to claim 1, wherein provided between the treatment chamber and the buffer chamber are at least two deflecting walls which deflect a flow direction of the gaseous medium towards the discharge opening.

9. The device according to claim 1, wherein at least one nozzle for cleaning the tank is provided in the tank.

10. The device according to claim 1 wherein at least one nozzle arranged in a stationary manner is provided in the buffer chamber.

11. The device according to claim 1, wherein the tank is arranged below the containers to be sterilized.

12. The device according to claim 1, wherein the discharge opening is arranged above a fill level of the liquid medium.

13. The device according to claim 1, wherein the discharge opening is adjoined by a discharge pipe for the gaseous medium, which extends partially through the tank.

14. The device according to claim 1, wherein the discharge opening is adjoined by a discharge pipe for the gaseous medium, which extends partially through the tank.

15. A device for sterilizing containers, comprising a treatment chamber for holding a sterilizing gaseous medium under predefined thermodynamic conditions, a tank for holding a level of liquid medium, a plurality of holding devices for holding the containers, wherein the holding devices are rotatable relative to at least one of the walls forming the treatment chamber, and a separating wall which protrudes into the tank below the level of liquid medium and rotatable relative to the tank, wherein a discharge opening, via which the gaseous medium can be discharged, is provided between the treatment chamber and the tank, and wherein a buffer chamber for the gaseous medium is provided between the treatment chamber and the tank, adapted to maintain the gaseous medium in the buffer chamber at a lower pressure than in the treatment chamber such that the gaseous medium may pass from the treatment chamber into the buffer chamber, wherein said discharge opening is adjoined by a discharge pipe for the gaseous medium, which extends partially through the tank.

16. The device according to claim 15, wherein the separating wall is arranged on a cover which covers the treatment chamber.

17. The device according to claim 16, wherein at least one nozzle for cleaning the buffer chamber is provided on the cover.

18. The device according to claim 15, wherein at least one nozzle for cleaning the tank is provided in the tank.

19. The device according to claim 15, wherein the discharge opening is arranged above a fill level of the liquid medium.

* * * * *

UNITED STATES PATENT AND TRADEMARK OFFICE
CERTIFICATE OF CORRECTION

PATENT NO. : 8,337,772 B2  
APPLICATION NO. : 12/681426  
DATED : December 25, 2012  
INVENTOR(S) : Laumer et al.

Page 1 of 1

It is certified that error appears in the above-identified patent and that said Letters Patent is hereby corrected as shown below:

In the Claims

Claim 1, Col. 7, line 34, "via which the gaseous via which the gaseous" should be --via which the gaseous--.

Signed and Sealed this  
Nineteenth Day of August, 2014

Michelle K. Lee  
*Deputy Director of the United States Patent and Trademark Office*